United States Patent [19]

Kobayashi

[11] Patent Number: 4,765,744

[45] Date of Patent: Aug. 23, 1988

[54] METHOD FOR TESTING A PHOTOMASK

[75] Inventor: Kenichi Kobayashi, Tokyo, Japan

[73] Assignee: Fujitsu Limited, Kawasaki, Japan

[21] Appl. No.: 22,249

[22] Filed: Mar. 5, 1987

Related U.S. Application Data

[60] Division of Ser. No. 861,669, May 7, 1986, abandoned, which is a continuation of Ser. No. 724,507, Apr. 19, 1985, abandoned, which is a continuation of Ser. No. 384,042, Jun. 1, 1982, abandoned.

[30] Foreign Application Priority Data

Jun. 1, 1981 [JP] Japan ................................ 56-82538

[51] Int. Cl.$^4$ ............................................. G01B 11/00
[52] U.S. Cl. ...................................... 356/398; 382/61
[58] Field of Search .................. 356/394, 398; 382/61

[56] References Cited

U.S. PATENT DOCUMENTS

| | | | |
|---|---|---|---|
| 3,847,346 | 11/1974 | Dolch | 382/61 |
| 3,852,573 | 12/1974 | Dolch | 382/61 |
| 4,065,212 | 12/1977 | Belleson et al. | 356/394 |

Primary Examiner—R. A. Rosenberger
Attorney, Agent, or Firm—Staas & Halsey

[57] ABSTRACT

A photomask comprises a tested pattern ($P_1$, $P_2$) and a synchronization pattern ($SP_1 \sim SP_8$). The synchronization pattern is used for synchronizing a scanning signal ($S_9$), obtained from the tested pattern, with a reference signal ($S_{10}$), based on a reference pattern data stored on a magnetic tape (7).

2 Claims, 5 Drawing Sheets

METHOD FOR TESTING A PHOTOMASK

This is a divisional of co-pending application Ser. No. 861,669 filed on May 7, 1986, which is a continuation of U.S. application Ser. No. 724,507, filed Apr. 19, 1985, now abandoned, and which is a continuation of U.S. application Ser. No. 384,042, filed June 1, 1982, now abandoned.

BACKGROUND OF THE INVENTION

The present invention relates to a photomask including a reticle, used in the manufacture of semiconductor devices.

In general, a photomask has a large number of high-resolution images. If a photomask has one or more defective images and is used in the manufacture of semiconductor devices, the manufacturing yield of semiconductor devices is reduced. Therefore, it is important to test the pattern of a photomask prior to the use thereof.

One conventional method for testing the pattern of a photomask is performed by determining whether or not a scanning signal obtained by scanning the pattern of the photomask is inconsistent with a reference scanning signal based on reference data stored in a storage unit such as a magnetic tape. In this case, the scanning of the pattern of a photomask is performed by moving the stage on which the photomask is mounted. Of course, it is necessary that the scanning signal obtained by scanning the pattern of the photomask be synchronized with the reference scanning signal read out of the magnetic tape. However, when the motion of the stage is reversed, it is difficult to synchronize the two scanning signals. The synchronization requires a highly accurate movement of the stage, thereby increasing the cost of a unit for testing a photomask.

SUMMARY OF THE INVENTION

It is, therefore, an object of the present invention to provide a photomask by which the cost of a unit for testing a photomask is reduced.

According to the present invention, there is provided a photomask comprising a test pattern; and a synchronization pattern for synchronizing a signal generated by scanning the test pattern with a reference signal based on reference pattern data.

BRIEF DESCRIPTION OF THE DRAWINGS

The present invention will be more clearly understood from the following description with reference to the accompanying drawings.

DESCRIPTION OF THE PREFERRED EMBODIMENT

From FIGS. 1 through 4, it is shown that if the pattern $P_1$ of a photomask 1 is dark, a dark synchronization pattern $SP_1$, $SP_2$, $SP_3$, or $SP_4$ is provided while, in FIGS. 5 through 8, if the pattern $P_2$ of the photomask 1 is light, a light synchronization pattern $SP_5$, $SP_6$, $SP_7$, or $SP_8$ is provided.

Figure 1:
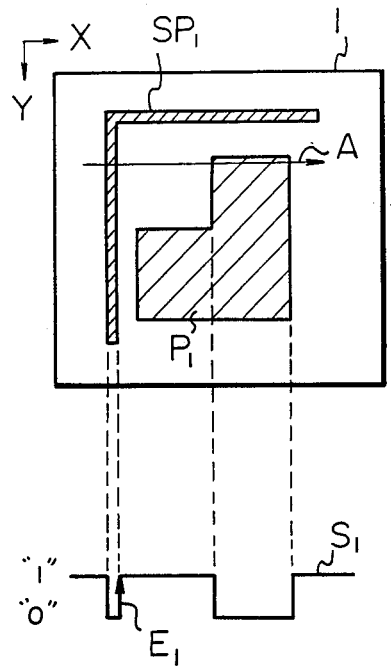
FIGS. 1 through 8 are diagrams of the patterns of a photomask according to the present invention.

In FIG. 1, the synchronization pattern $SP_1$ is provided on the left side of the pattern $P_1$ as well as the upper side thereof. In this case, the upper side portion of the pattern $SP_1$ is used for detecting the first position in the Y direction. Therefore, when scanning is performed in the X direction as indicated by the arrow A, a scanning signal $S_1$ is obtained. If the signal $S_1$ is a logical "0" level, it represents "dark" while a logical "1" level represents "light". By using the rising edge $E_1$, which is due to the presence of the synchronization pattern $SP_1$, a comparison of the scanning signal $S_1$ and the reference scanning signal is initiated. Similarly, in FIG. 5, by using the falling edge $E_5$, a comparison of the scanning signal $S_5$ and the reference scanning signal is initiated.

Figure 2:
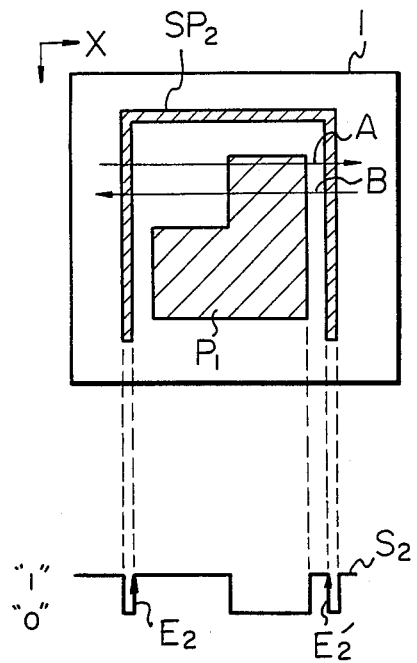

In FIG. 2, the synchronization pattern $SP_2$ is provided on three sides of the pattern $P_1$. Therefore, when scanning is performed in a traverse direction as indicated by the arrow A or B, a scanning signal $S_2$ is obtained. By using the rising edge $E_2$ (or $E_2'$) due to the presence of the synchronization pattern $SP_2$, a comparison of the scanning signal $S_2$ and the reference scanning signal is initiated. Similarly, in FIG. 6, by using the falling edge $E_6$ (or $E_6'$), a comparison of the scanning signal $S_6$ and the reference scanning signal is initiated.

Figure 3:
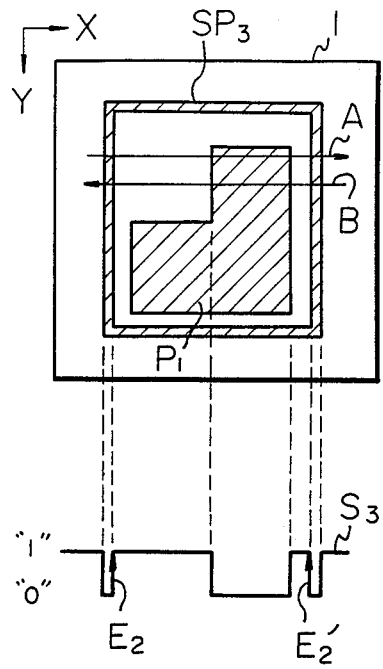
Figure 7:
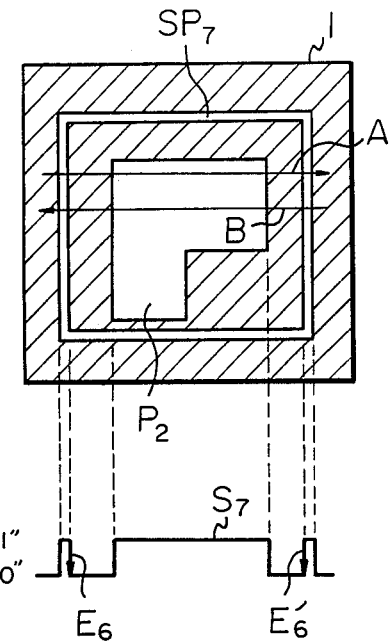

In FIG. 3, the synchronization pattern $SP_3$ is provided along the periphery of the pattern $P_1$, and in FIG. 7, the synchronization pattern $SP_7$ is also provided along the periphery of the pattern $P_2$. In this case, the lower side portion of the synchronization pattern $SP_3$ (or $SP_7$) is used for detecting the last position in the Y direction.

Figure 4:
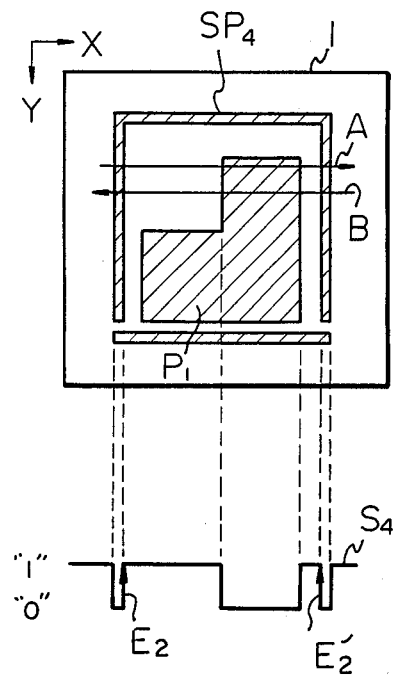
Figure 5:
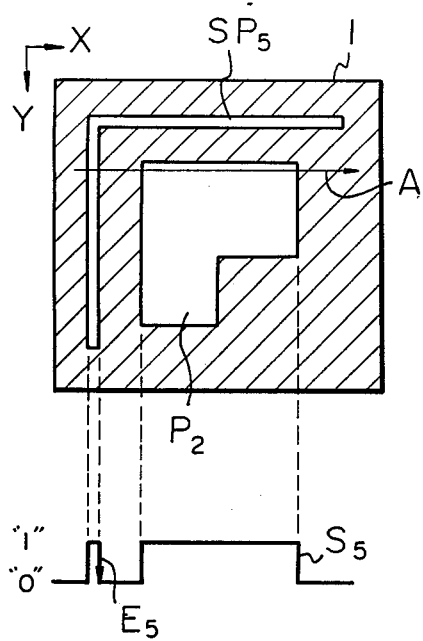
Figure 6:
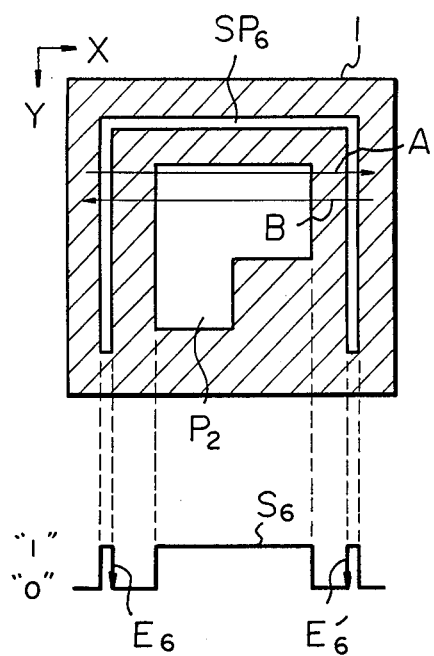
Figure 8:
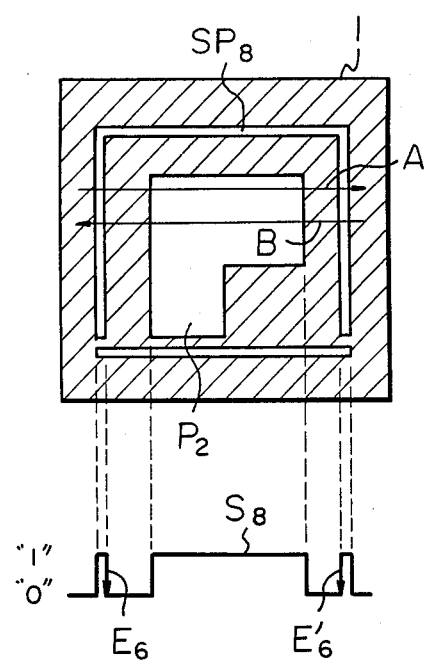

In FIGS. 4 and 8, the synchronization patterns $SP_4$ and $SP_8$ are asymmetrical in the Y direction. That is, discontinuities are present in the lower side of the patterns $SP_4$ and the discontinuities $SP_8$ and prevent the photomask 1 from being mounted upside down on a stage (not shown).

Figure 9:
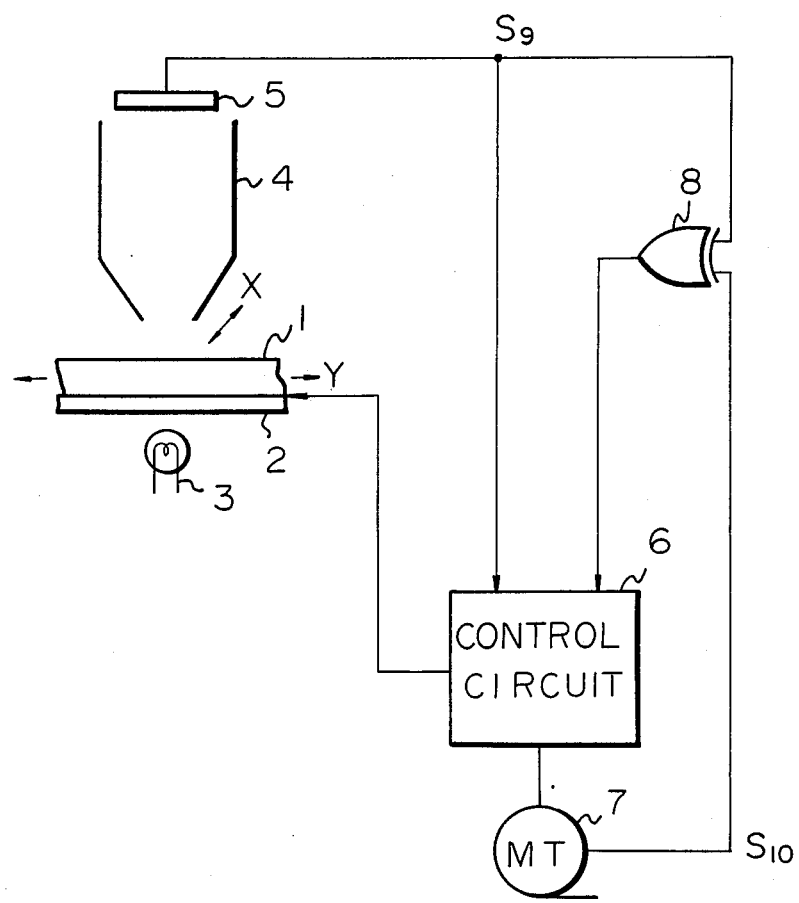
FIG. 9 is a block circuit diagram of a unit for testing the pattern of a photomask according to the present invention.

FIG. 9 is a block diagram illustrating a unit for testing the pattern of a photomask according to the present invention. In FIG. 9, a photomask 1 is mounted on a stage 2. A light source 3 is located on one side of the photomask 1 while an optical system (lens) 4 and a photoelectric converter unit 5 which comprises, for example, one or more image sensors arranged on the other side of the photomask 1. The stage 2 is driven by a control circuit 6. Reference numeral 7 indicates a magnetic tape for storing reference pattern data and reference numeral 8 indicates an exclusive OR circuit which serves as a comparison unit for comparing the scanning signal $S_9$ with the reference signal $S_{10}$ generated from the magnetic tape 7. Note that, in this case, the scanning signal $S_9$ is a digital signal.

The control circuit 6 comprises, for example, a microcomputer which comprises a central processing unit (CPU), a read-only memory (ROM) for storing constants, programs, and the like, and a random access memory (RAM) for storing intermediate data and the like.

The operation of the unit of FIG. 9 will now be explained. First, the control circuit 6 drives the stage 2 in the X direction so as to detect a synchronization pattern, for example, the synchronization pattern $SP_1$ of FIG. 1, in the scanning signal $S_9$. Next, when the edge $E_1$ of FIG. 1 is detected, the control circuit 6 performs a read operation upon the magnetic tape 7, which, in turn, generates the reference signal $S_{10}$ based on the reference pattern data stored in the magnetic tape 7. That is, each time such read operation is performed, the control circuit 6 shifts the stage 2 a predetermined distance. When the exclusive OR circuit 8 detects an inconsistency between the two signals $S_9$ and $S_{10}$, the control circuit 6 writes the position of the stage 2 into the RAM of the control circuit 6. That is, in the RAM of the control circuit 6, a failure map for indicating the position of the defective areas is formed.

In FIG. 9, the motion of the stage 2 follows the read operation of the magnetic tape 7 and therefore a high accuracy for the movement of the stage 2 becomes unnecessary.

In addition, the synchronization pattern, particularly the upper portion thereof, is used for detecting the slope of the photomask 1. If the photomask 1 is inclined, a state of inconsistency often occurs. Such a state is detected by the control circuit 6. Further, the synchronization pattern can also be used for monitoring the exposure process, the etching process, and the like in the manufacture of a photomask, particularly in the case where the photomask has a complex pattern.

As was explained hereinbefore, the photomask according to the present invention is advantageous in that a high accuracy of movement of the stage is unnecessary, thereby reducing the cost of a unit for testing a photomask.

I claim:

1. A method for testing a photomask comprising the steps of:
    (a) forming a synchronization pattern surrounding a photomask pattern including first through fourth linear synchronization patterns having an elongated shape formed continuously in first and second directions, the first linear synchronization pattern extending in the first direction, the second linear synchronization pattern formed continuously from an end of the first linear synchronization pattern and extending in the second direction which is perpendicular to the first direction, the third linear synchronization pattern formed continuously from an end of the second linear synchronization pattern and extending in the first direction so as to be parallel to the first linear synchronization pattern, and the fourth linear synchronization pattern formed parallel to the second linear synchronization pattern, a space being formed between each of the first and third linear synchronization patterns and the fourth linear synchronization pattern;
    (b) storing a reference data, corresponding to a normal mask pattern, into a first storing means;
    (c) mounting the photomask on a stage;
    (d) optically scanning the first through fourth linear synchronization patterns and the photomask by driving the stage along the second direction and generating a scanning signal including a synchronization signal for each scanning operation, for detecting whether the photomask is upside down by detecting the space between the fourth linear synchronization pattern and each of the first and third linear synchronization patterns, the scanning direction being reversed at the end of each scanning operation;
    (e) detecting a start of a pattern generating area along the second direction by driving the stage along the first direction;
    (f) reading the reference data corresponding to the scanning signal from the first storing means in response to the synchronization signal, for generating a reference signal;
    (g) comparing the scanning signal with the reference signal; and
    (h) storing a position of the stage into a second storing means when the scanning signal is inconsistent with the reference signal, to form a failure map in the second storing means.

2. A photomask as set forth in claim 1, wherein said step (a) includes forming the first through fourth linear synchronization patterns on the periphery of the photomask.

* * * * *

UNITED STATES PATENT AND TRADEMARK OFFICE
CERTIFICATE OF CORRECTION

PATENT NO. : 4,765,744
DATED : AUGUST 23, 1988
INVENTOR(S) : KENICHI KOBAYASHI

It is certified that error appears in the above-identified patent and that said Letters Patent is hereby corrected as shown below:

Col. 2, line 32, "$SP_4$ and the discontinuities $SP_8$" should be --$SP_4$ and $SP_8$ and the discontinuities--.

Signed and Sealed this

Third Day of January, 1989

Attest:

DONALD J. QUIGG

Attesting Officer

Commissioner of Patents and Trademarks